(12) United States Patent
Lyon et al.

(10) Patent No.: US 10,349,923 B2
(45) Date of Patent: Jul. 16, 2019

(54) FEMALE URINE STRAINERS AND SAMPLERS

(71) Applicant: Timothy L. Lyon, South Jordan, UT (US)

(72) Inventors: Timothy L. Lyon, South Jordan, UT (US); Brenda Lyon, South Jordan, UT (US)

( * ) Notice: Subject to any disclaimer, the term of this patent is extended or adjusted under 35 U.S.C. 154(b) by 0 days.

(21) Appl. No.: 15/943,549

(22) Filed: Apr. 2, 2018

(65) Prior Publication Data

US 2018/0303465 A1     Oct. 25, 2018

Related U.S. Application Data

(60) Provisional application No. 62/489,251, filed on Apr. 24, 2017.

(51) Int. Cl.
    *B01D 29/13*          (2006.01)
    *A61B 10/00*          (2006.01)

(52) U.S. Cl.
    CPC ............ *A61B 10/007* (2013.01); *B01D 29/13* (2013.01)

(58) Field of Classification Search
    CPC .............................. A61B 10/007; B01D 29/13
    See application file for complete search history.

(56) References Cited

U.S. PATENT DOCUMENTS

| | | | | |
|---|---|---|---|---|
| 3,131,403 A | * | 5/1964 | Hill | A61B 10/007 4/144.3 |
| 3,137,010 A | * | 6/1964 | Ross | A61B 10/0038 4/483 |
| 3,432,998 A | * | 3/1969 | Downey | A47L 9/1454 137/512.5 |
| D285,487 S | | 9/1986 | Tjernagel | |
| 4,738,673 A | | 4/1988 | Shepard | |
| 4,815,151 A | * | 3/1989 | Ball | A61F 5/4556 4/144.1 |
| 5,492,220 A | | 2/1996 | Estay | |
| 5,772,644 A | | 6/1998 | Bark et al. | |
| D456,989 S | | 5/2002 | Yang | |
| 6,719,951 B1 | | 4/2004 | Griffith | |
| 6,775,852 B1 | | 8/2004 | Alvarez et al. | |
| 6,973,678 B2 | | 12/2005 | Jones | |

(Continued)

OTHER PUBLICATIONS

Cook Medical Product Webpage, Disposable Stone Strainer, https://www.cookmedical.com/products/uro_dss_webds/.

(Continued)

*Primary Examiner* — Chester T Barry
(74) *Attorney, Agent, or Firm* — Paul C. Oestreich; Eminent IP, P.C.

(57) ABSTRACT

The present invention includes strainers used to gather solids from voided urine. Embodiments include urinary bowl strainers, hand-held strainers and disposable hand-held urine strainers, all of which are particularly useful for gathering kidney stones passed in urine that are intended for verification of passing said kidney stones, and for laboratory analysis which may be used to guide clinical treatment to prevent recurrent kidney stone formation. Embodiments of disposable urine samplers are also disclosed. The embodiments of urine strainers and samplers disclosed herein are particularly adapted for use by female patients, though male patients may also use the devices.

13 Claims, 17 Drawing Sheets

(56) References Cited

U.S. PATENT DOCUMENTS

| | | | |
|---|---|---|---|
| 7,128,352 B1 | 10/2006 | Phippen | |
| 7,244,236 B2 | 7/2007 | Merkle | |
| 8,091,848 B1 | 1/2012 | Reed | |
| 8,465,440 B1 | 6/2013 | Grayson | |
| 8,690,794 B1* | 4/2014 | Gallardo | A61B 10/007 |
| | | | 600/562 |
| D706,947 S | 6/2014 | Hooper | |
| D773,657 S | 12/2016 | Meloff et al. | |
| 9,662,094 B2 | 5/2017 | Meloff et al. | |
| 2014/0360390 A1* | 12/2014 | Frick | B41C 1/14 |
| | | | 101/128.21 |
| 2016/0051445 A1* | 2/2016 | Sidorsky | A61J 1/00 |
| | | | 435/309.1 |
| 2018/0126661 A1* | 5/2018 | Dunlap | B29C 65/18 |

OTHER PUBLICATIONS

Amazon.com Webpage, Covidien 2110SA, Urine Calculi Strainer, https://www.amazon.com/Urine-Calculi-Stralner_Covidien-2110SA/dp/B0064Q2EEO.
Maddak SP Ableware Webpage, Collecting Funnel with Filter, http://www.maddak.com/collecting-funnel-with-filter-p-27870.html.
Vitality Medical Webpage, McKesson Calculi Strainer, http://www.vitalitymedical.com/calculi-strainer.html.
Amazon.com Webpage, Specimen Collection Unit, https://amazon.com/Specimen-Collection-Unit-QTY-1/dp/B001lSHH4U/ref=sr_1_7/ . . . .
Amazon.com Webpage, CareFull Catch Specimen Holder (10 Pack), https://www.amazon.com/CareFull-Catch-specimen-holder-pack/dp/B01H2MOZDQ.

* cited by examiner

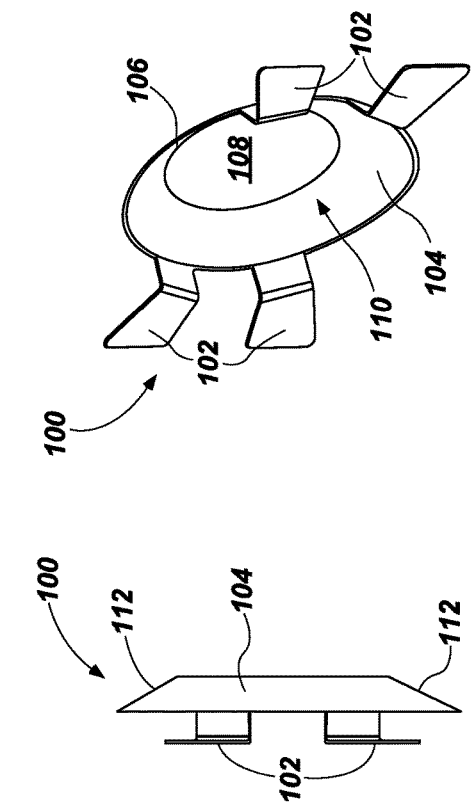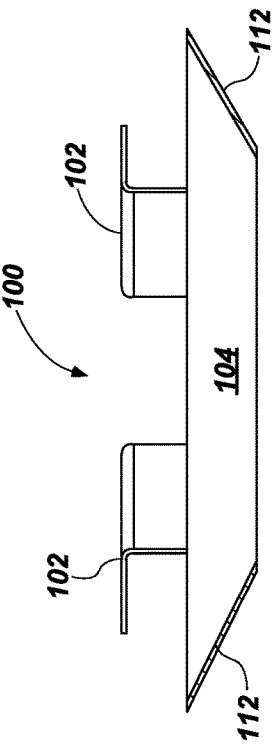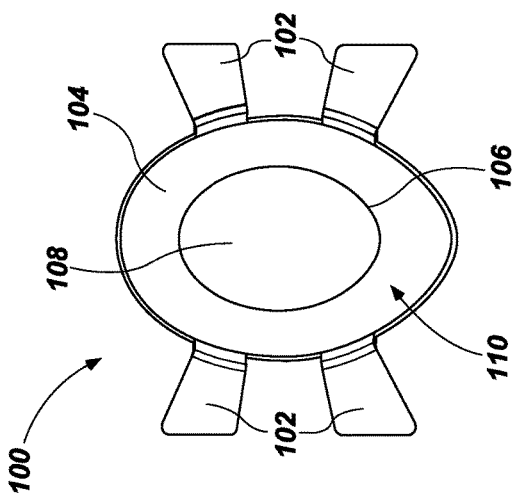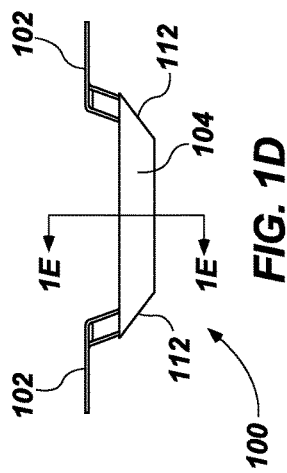

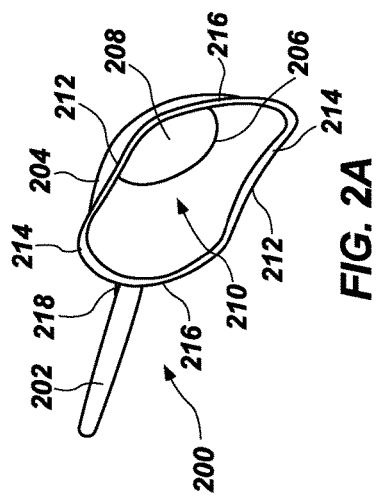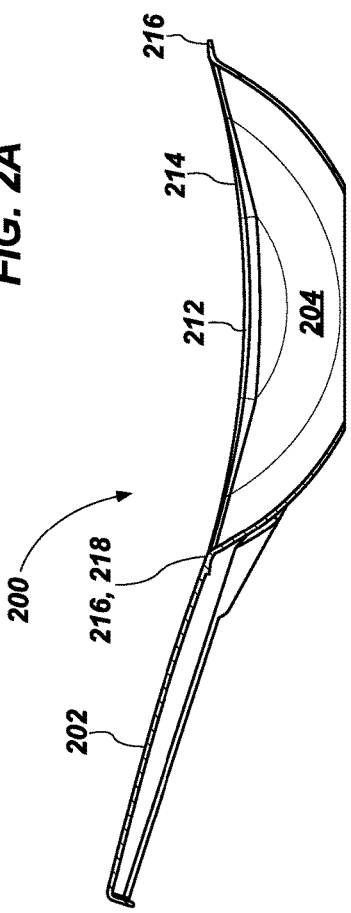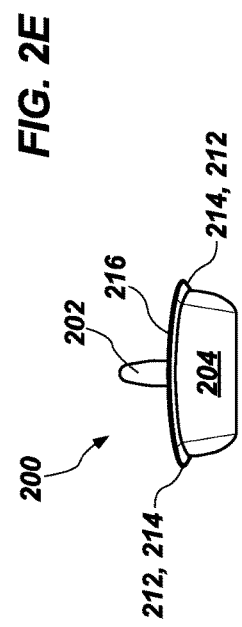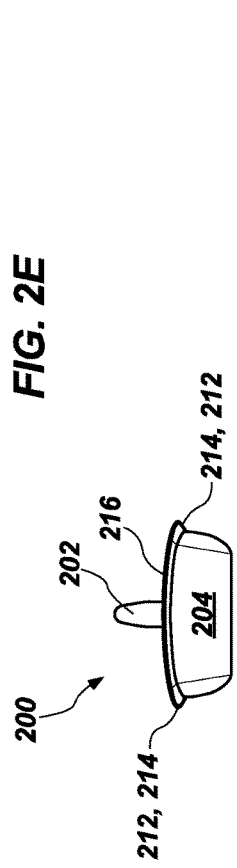
FIG. 2A
FIG. 2B
FIG. 2C
FIG. 2D
FIG. 2E

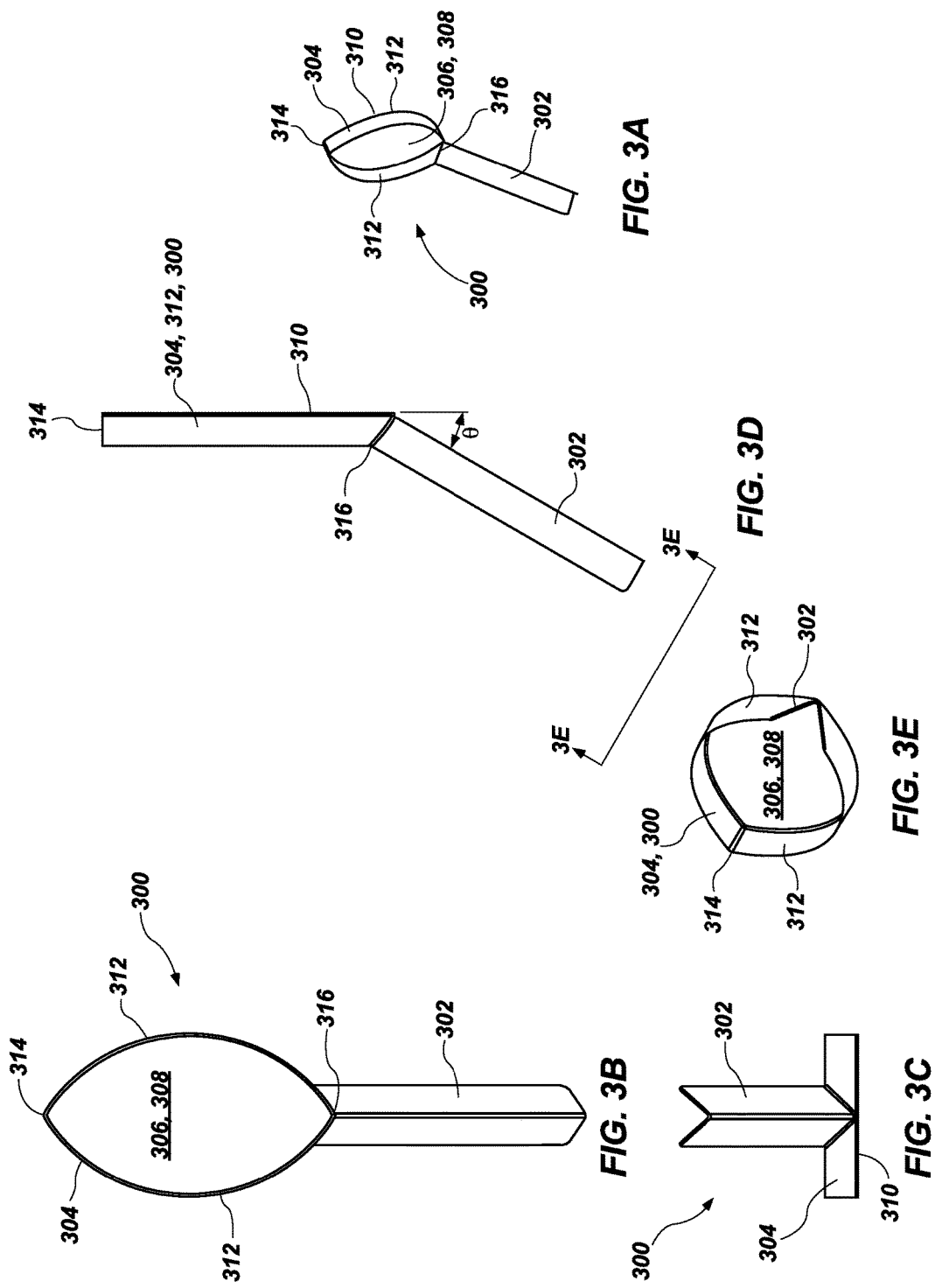

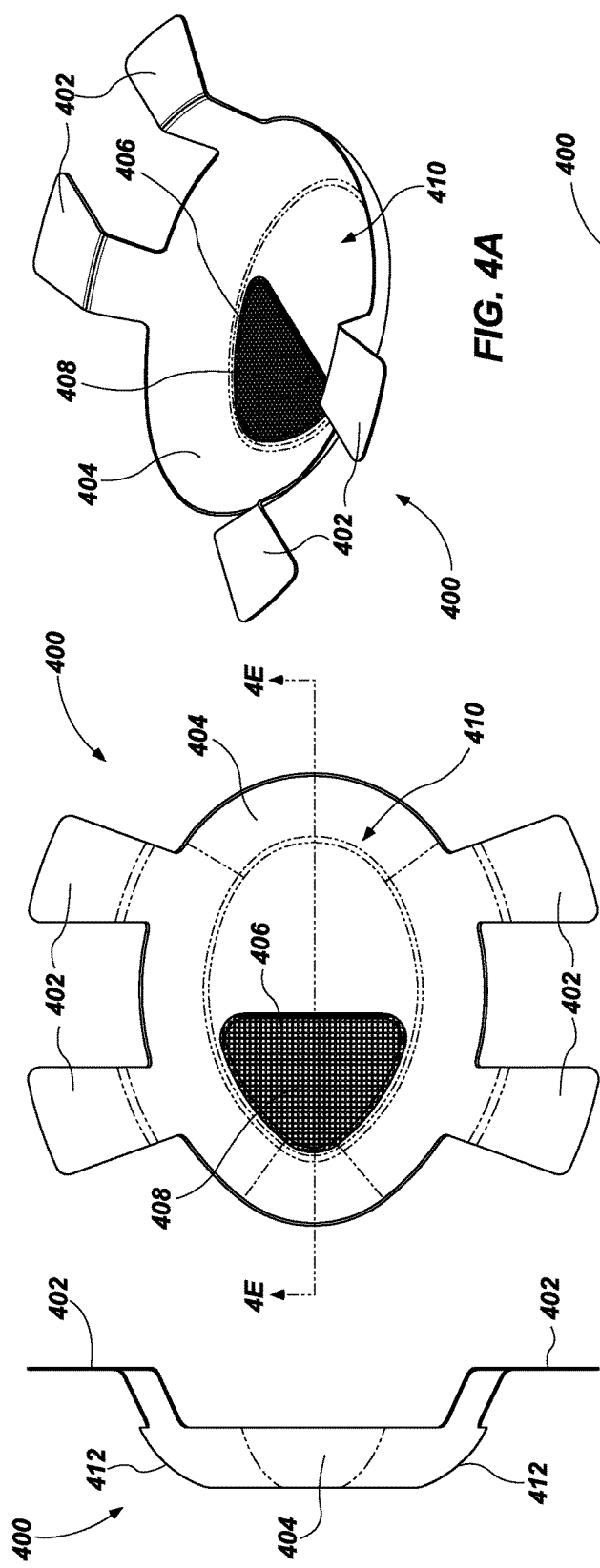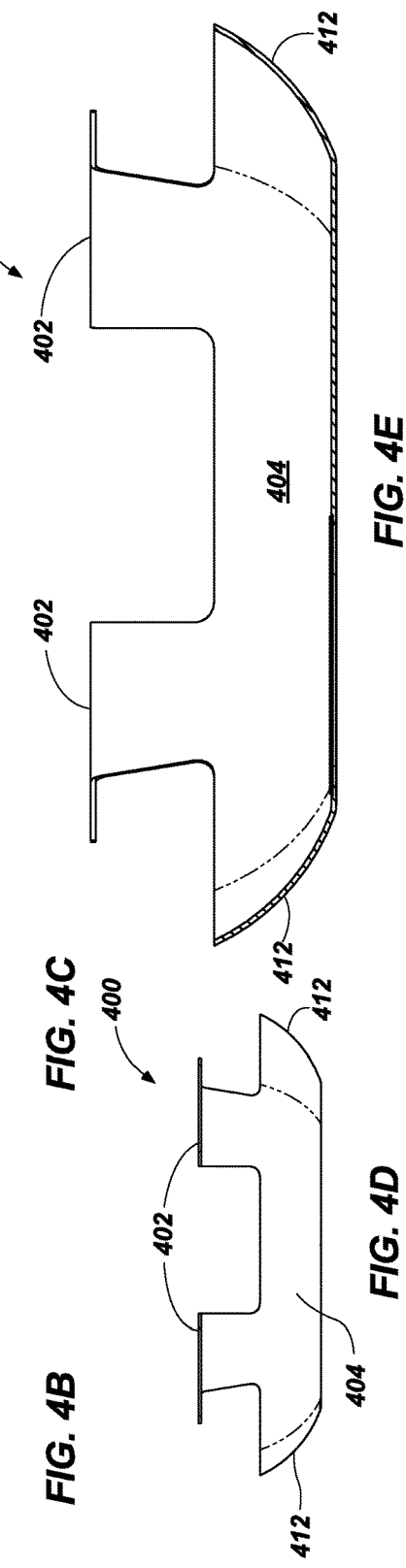

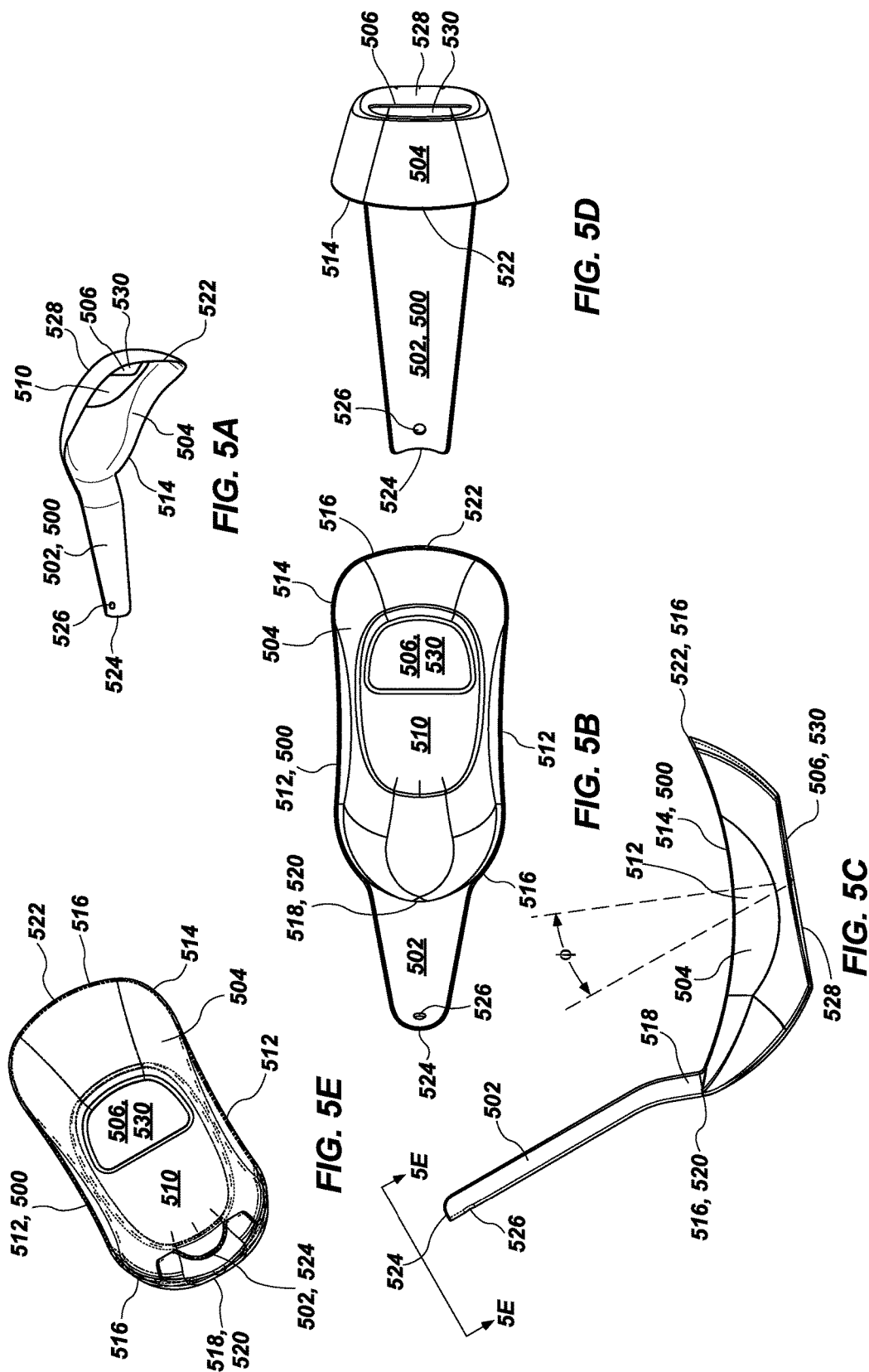

FEMALE URINE STRAINERS AND SAMPLERS

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

CROSS-REFERENCE TO RELATED APPLICATIONS

This US non-provisional utility patent application claims benefit and priority to U.S. provisional patent application No. 62/489,251 filed on Apr. 24, 2017, titled "FEMALE URINE STRAINER", the contents of which are incorporated by reference as if fully set forth herein for all purposes.

BACKGROUND OF THE INVENTION

Field of the Invention

The present invention relates generally to urine strainers used by patients with kidney stones and urine samplers. More particularly, this invention relates to urine strainers designed for the unique physical needs of female users and also urine samplers for use by anyone that needs to produce a urine sample.

Description of Related Art

There are many potential causes of kidney stone formation. In general they result from a super concentration of chemicals in the urine that result in crystals being formed. This may be brought on by one or more of the following: a family genetic predisposition to form stones, an excess of calcium or certain other minerals in the diet (sometimes due to local geographic water or soil conditions), intake of excess uric acid, certain medications, Vitamin C, or Vitamin D, a diet of fruits and vegetables high in oxalate (a by-product of metabolism), long term dehydration (possibly due to inadequate intake of fluids) and its resulting concentration of urine, urinary infection, living in an area where high temperatures cause sweating and loss of fluids, or possibly, just leading a sedentary (low physical activity) lifestyle.

Kidneys eliminate byproducts of metabolism. This means that kidneys are constantly collecting the major ingredients for kidney stones, including: calcium, oxalate, and uric acid. Ideally these minerals are kept in suspension until they are passed out of the body. Individuals who have excess metabolic by-products in insufficient fluid (urine) are particularly prone to kidney stone formation.

The excess concentration of metabolic byproducts in the urine can cause these minerals to move out of suspension and crystallize. These small crystals that precipitate out of the super saturated urine will usually pass out through the urinary tract, but they may begin to clump together. Any existing crystal makes it easier for other crystals to form. If they stay in the kidney very long, the crystals gradually grow larger and larger until they become a kidney stone so large that it cannot pass comfortably through the urinary tract.

Since kidney stones may contain a variety of crystalline and noncrystalline materials it is important to know the composition of a kidney stone in order to guide clinical decisions. Although urine composition provides information on the possible composition of a patient's stone, this is not perfectly predictive of the stone type and, at times, can be misleading. Thus, instructing the patient to retrieve a passed stone or instructing the urologist, who is performing a stone-related procedure, to save and send a stone fragment for analysis is an important part of the approach to prevent recurrent stone formation. The stone composition may also influence the choice of urologic intervention.

The most common crystalline materials found in kidney stones may include calcium oxalate, calcium phosphate, uric acid, and struvite. It is not uncommon for a stone to contain more than one crystalline component. Noncrystalline materials found in kidney stones may include proteins and blood. Some laboratories report the composition of the infection nidus (if present) separately from the composition of the body of the stone.

Thus, patients with kidney stones are frequently asked by their urologists to collect kidney stones as they are passed in order to perform a laboratory analysis on their composition. Most conventional devices used to gather kidney stones are little more than a funnel shaped strainer with a fine mesh to allow urine to pass through while holding back the kidney stones via the fine mesh. However, such conventional urine strainers tend to be much easier for male patients than female patients.

As one can imagine it is much easier for men to direct a urine stream into a strainer than it is for women. Merely obtaining a urine sample also presents difficulties for women for similar reasons. Accordingly, there exists a need in the art for urine strainers and samplers better suited for use by female patients.

BRIEF SUMMARY OF THE INVENTION

The present invention includes embodiments of strainers used to gather solids from voided urine. Particular embodiments include urinary bowl strainers, hand-held strainers and disposable hand-held urine strainers, all of which are particularly useful for gathering kidney stones passed in urine that are intended for verification of passing said kidney stones, and for laboratory analysis which may be used to guide clinical treatment to prevent recurrent kidney stone formation.

The present invention further includes embodiments of disposable urine samplers which are used to obtain urine samples. The embodiments of disposable urine samplers generally include a handle leading to a urine cup receptacle. The embodiments of urine samplers disclosed herein are used by patients who have been instructed or otherwise need to produce a urine sample in a urine sample cup. The embodiments of urine samplers disclosed herein help prevent accidental urination on the hands or fingers of the user during the urine sampling process.

The embodiments of urine strainers and samplers disclosed herein are particularly adapted for use by female patients, though male patients may also use the devices. Because each embodiment disclosed may be used by either gender, they may find universal application as urine strainers and samplers. The universal urine strainers and samplers disclosed herein are thus advantageous over conventional strainers and samplers that are available in the market to date, which are generally convenient only for males.

Additional features and advantages of the invention will be apparent from the detailed description which follows, taken in conjunction with the accompanying drawings, which together illustrate, by way of example, features of embodiments of the present invention.

BRIEF DESCRIPTION OF THE SEVERAL VIEWS OF THE DRAWINGS

The following drawings illustrate exemplary embodiments for carrying out the invention. Like reference numerals refer to like parts in different views or embodiments of the present invention in the drawings.

FIGS. 1A-1E are perspective, side, top, front and cross-sectional views, respectively, of an embodiment of a of urinary bowl strainer, according to the present invention.

FIGS. 2A-2E are perspective, top, side, front and cross-sectional views, respectively, of an embodiment of a hand-held urine strainer, according to the present invention.

FIGS. 3A-3E are perspective, top, rear, side and handle perspective views, respectively, of an embodiment of a disposable hand-held urine strainer, according to the present invention.

FIGS. 4A-4E are perspective, front, top, side, front, handle and cross-sectional views, respectively, of another embodiment of a urinary bowl strainer, according to the present invention.

FIGS. 5A-5E are perspective, top, side, front and handle-edge views, respectively, of another embodiment of a hand-held urine strainer, according to the present invention.

DETAILED DESCRIPTION OF THE INVENTION

Figure 4F:
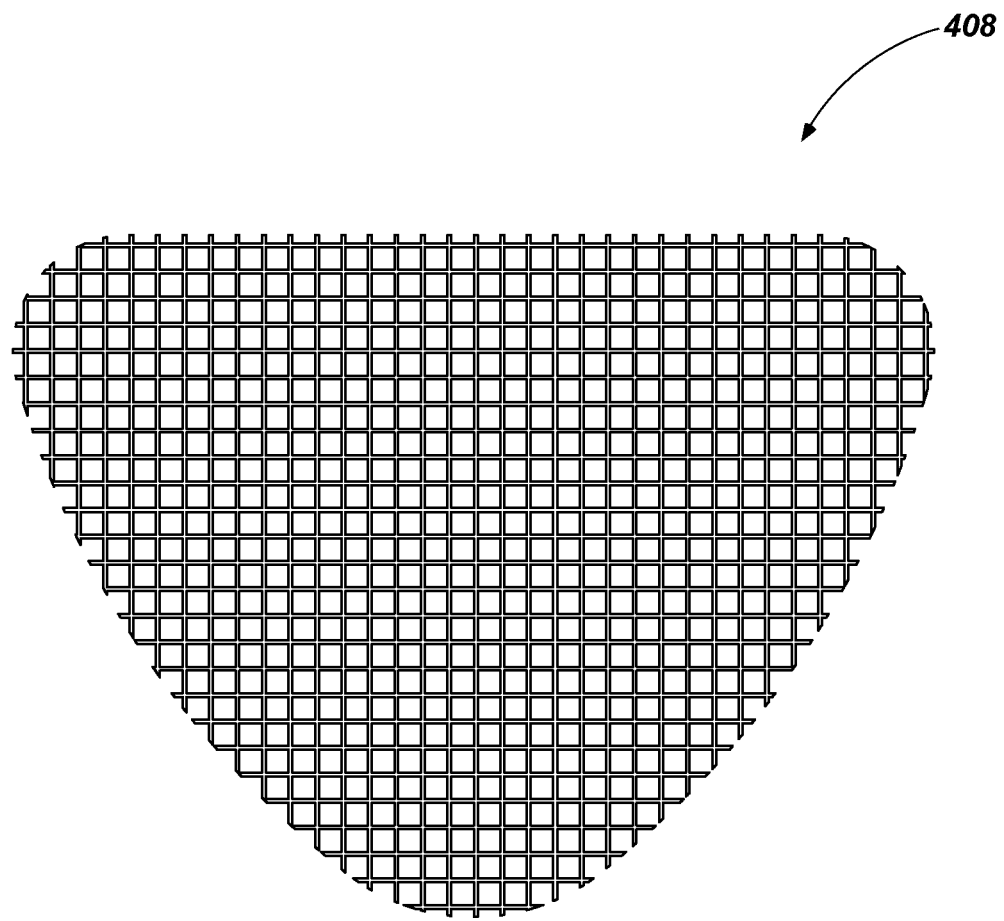
FIG. 4F is a plan view of an embodiment of a fine mesh feature of the embodiment of a urinary bowl strainer shown in FIGS. 4A-4E, according to the present invention.

Embodiments of the present invention include a disposable urine strainer, a bowl strainer and a hand-held strainer, all of which are particularly useful for gathering kidney stones passed in urine that are intended for laboratory analysis to further guide clinical treatment to prevent recurrent kidney stone formation. An embodiment of a disposable urine sampler is also disclosed. The embodiments of urine strainers and samplers disclosed herein are particularly adapted for use by female patients, but may also be used by male patients.

FIGS. 1A-1E are perspective, side, top, front and cross-sectional views, respectively, of an embodiment of a urinary bowl strainer 100, according to the present invention. Bowl strainer 100 may be configured for use with any standard toilet (not shown). More particularly, the embodiment of a bowl strainer 100 is configured for placement between the toilet bowl and toilet seat (neither shown). Bowl strainer 100 is ideal for use at home where the patient may spend considerable time and experience multiple voids, and where it may be most convenient to gather passed kidney stones. Furthermore, the embodiment of a bowl strainer 100 shown in FIGS. 1A-1E is easy for female patients to use because being seated is the conventional female method for voiding urine.

Bowl strainer 100 may be round or oval (as shown in FIG. 1C) in shape, fitting at least partially inside the radiance of a standard round or oblong toilet. Bowl strainer 100 may include a plurality of support members 102, which can serve as handles when placing or retrieving the bowl strainer 100 from its position on a toilet (not shown). These support members 102 may be placed directly along the top of the toilet bowl (not shown) after the lid and toilet seat (neither shown) have been raised, and the toilet seat can be positioned on top of the support members 102 to hold the bowl strainer 100 in place during use. Using this particular embodiment of a bowl strainer 100, there is no requirement for the user to hold or manage the bowl strainer 100 while effecting void. The center (shown generally at arrow 110) of the bowl strainer 100 device is generally recessed and comprised of a bowl-shaped frame 104 with an opening 106 covered by a flexible fine thin mesh 108 to allow for fluid (urine) to pass through, while retaining any items contained in the urine stream to be retained inside the bowl strainer 100.

Bowl strainer 100 may be formed of lightweight plastic or other suitable materials that are washable and re-usable as needed. Bowl strainer 100 may also be made of disposable materials for singular use in hospital, clinical or home use. The bowl-shaped frame 104 may have straight line cross-section 112 as shown in the illustrated embodiment of a bowl strainer 100 in FIGS. 1B, 1D and 1E. However, various other cross-sections, for example and not by way of limitation, rounded or curved (see, e.g., 412 in FIGS. 4B, 4D and 4D and discussion below), according to other contemplated embodiments.

FIGS. 2A-2E are perspective, top, side, front and cross-sectional views, respectively, of an embodiment of a hand-held urine strainer 200, according to the present invention. Hand-held urine strainer 200 is configured for use while standing or squatting over a toilet bowl (not shown). Hand-held urine strainer 200 may be used by male and female patients. But, because of its shape, hand-held urine strainer 200 is particularly adapted for use by female patients. The hand-held urine strainer 200 is sized to be portable and is configured to reusable by simply washing in water. Additional features of the embodiment of hand-held strainer 200 follow.

Hand-held urine strainer 200 may have a rounded-rectangle-shaped rim 214 at the top of a generally bowl-shaped frame 204 as viewed from the top in FIG. 2B. The rounded-rectangular-shaped rim 214 includes two opposed convex lips 216 and two opposed concave lips 212. The lips 212 and 216 of rim 214 are rounded and not sharp-edged. The two opposed concave lips 212 are specially adapted to fit, and may be held, between the thighs of a female patient during urination. Hand-held urine strainer 200 may further include a protruding handle 202 extending from one of the two opposed convex lips 216. The hand-held urine strainer 200 is configured to gather urine inside the rim 214 and guide it toward the recessed area in the center 210 of the hand-held urine strainer 200.

The handle 202 may be used by the patient to control the placement of the hand-held strainer 200 during use. Hand-held urine strainer 200 may further include a generally bowl-shaped frame 204 extending from the rim 214 down to a circular opening 206. The circular opening 206 located within the recessed center 210 may be comprised of a flexible thin fine mesh for straining fluid voids. Handle 202 may extend from rim 214 and handle base 218. Handle 202 may be configured with any suitable shape and length according to various embodiments. More particularly, the shape and length of handle 202 is specifically designed for female patients to avoid urinating on their own hand, or other body part, or on the toilet, or rim thereof, and to collect any items passed through the urine stream such as kidney stones for analysis.

FIGS. 3A-3E are perspective, top, rear, side and handle perspective views, respectively, of an embodiment of a disposable hand-held urine strainer 300, according to the present invention. Like the hand-held urine strainer 200 embodiment, the disposable hand-held urine strainer 300 is also portable. Disposable hand-held urine strainer 300 is configured for use while standing or squatting over a toilet bowl (not shown). Disposable hand-held urine strainer 300 may be used by male and female patients. But, because of its shape, Disposable hand-held urine strainer 300 is particularly adapted for use by female patients. The opposed curved walls 312 together form a football-shaped cross-sectioned frame 304. The football cross-sectioned frame 304 has a football cross-sectioned opening 306 that is covered at the bottom end 310 by a flexible fine thin mesh 308. The opposed curved walls 312 are intentionally narrow relative to the overall length from tip 314 to handle base 316 in order to allow the disposable hand-held urine strainer 300 to be close to the inner thighs of female patients during use. Because of its lightweight construction, disposable hand-held urine strainer 300 is further configured to be disposable and not reused.

Disposable hand-held urine strainer 300 is a lightweight portable device for use in straining fluids and capturing any items contained in the urine stream such as kidney stones for analysis. Disposable hand-held urine strainer 300 may be constructed of any suitable disposable materials, for example and not by way of limitation, lightweight milled paper or cardboard. According to one embodiment, disposable hand-held urine strainer 300 may be supported by thin wire located at the vertex, or fold lines, or bottom end of the milled paper to ensure flexibility for handling, according to various embodiments of the present invention.

The center opening 306 may be any suitable shape, for example and not by way of limitation, football cross-sectioned or oval in shape as depicted in FIGS. 3A, 3B and 3E. The center opening 306 at the recessed bottom 310 may be covered with a flexible fine thin mesh 308. A handle 302 may be attached to the football cross-sectioned frame 304 at the handle base 316 and can be folded for transport and easy storage. When the handle 302 is unfolded and out, it gives the user ample length for holding and placement of the strainer 300 inside the toilet bowl and/or between the user's thighs, to collect the void. The handle length, orientation and strainer shape are specifically designed for female use, to avoid the female patient getting any urine on their hand or elsewhere while performing urination. For example, the handle 302 may be disposed at any suitable angle, e, relative to frame 304 as shown in FIG. 3E. Once collected, any items retained inside the mesh portion can be retained in a separate bag or container for transport to a medical professional, or analyzed by the user and then discarded with the disposable hand-held urine strainer 300.

FIGS. 4A-4E illustrate another embodiment of a urinary bowl strainer 400, according to the present invention. More particularly, FIGS. 4A-4E are perspective, front, top, side and cross-sectional views, respectively, the embodiment of a urinary bowl strainer 400, similar to the embodiment of bowl strainer 100 shown in FIGS. 1A-1E. Bowl strainer 400 may also be configured for use with any standard toilet (not shown). Bowl strainer 400 is configured for placement between the toilet bowl and toilet seat (neither shown). Bowl strainer 400 is ideal for use at home where the patient may spend considerable time, experience multiple voids, and where it may be most convenient to gather passed kidney stones. Furthermore, the embodiment of a bowl strainer 400 shown in FIGS. 4A-4E is easy for female patients to use because being seated is the conventional female method for voiding urine.

Bowl strainer 400 may be round or oval (as shown in FIGS. 4A and 4C) in shape, fitting at least partially inside the radiance of a standard round or oblong toilet. Bowl strainer 400 may include a plurality of support members 402 (four shown), which can serve as handles when placing or retrieving the bowl strainer 400 from its position on a toilet (not shown). These support members 402 may be placed directly along the top of the toilet bowl (not shown) after the lid and toilet seat (neither shown) have been raised followed by the toilet seat positioned on top of the support members 402 to hold the bowl strainer 400 in place during use. Using bowl strainer 400, there is no requirement for the user to hold or manage the bowl strainer 400 while effecting void. The center, shown generally at arrow 410 (FIGS. 4A and 4C) of the bowl strainer 400 includes a generally recessed and bowl-shaped frame 404 with an opening 406 covered by a flexible fine thin mesh 408 to allow for fluid (urine) to pass through, while retaining any items contained in the urine stream to be retained inside the bowl strainer 400. Note that the opening 406 and mesh 408 are both smaller than opening 106 and mesh 108 in bowl strainer 100. This smaller sizing in the embodiment of bowl strainer 400 may have the advantage of lower cost and yet still maintains the functionality versus the embodiment of bowl strainer 100.

FIG. 4F is a plan view of an embodiment of the flexible fine thin mesh 408 of the embodiment of a urinary bowl strainer 400 shown in FIGS. 4A-4E, according to the present invention. Mesh 408 may be formed of any suitable material that allows fluid (urine) to pass through the mesh 408 and into the toilet bowl or other urine receptacle, while retaining any items (kidney stones, etc.) contained in the urine stream. According to one embodiment, mesh 408 may be formed of 800 micron polypropylene mesh having 58% open area, with hole size 0.032"×0.032" and having thickness, 0.016". It will be understood that the particular dimensions of mesh 408 illustrated in FIG. 4F are configured to allow mesh 408 to cover opening 406. According to the illustrated embodiments, opening 406 and its corresponding mesh 408 are generally "guitar pick", or roughly D-shaped, in plan view. However, it will further be understood that the particular shape of opening 406 and its corresponding mesh 408 may be of any suitable shape. Mesh 408 may be adhered to bowl strainer 400 in any manner known to those skilled in the art including, for example and not by way of limitation, adhesive, thermal fusing, tape, etc.

One additional advantage of the embodiment of bowl strainer 400 versus bowl strainer 100 is that the bottom portion that does not have mesh 408 can be used to obtain a stool sample if properly placed on a toilet while allowing urine to strain out. A urine strained stool sample may also be obtained using the embodiment of bowl strainer 100, however mesh 108 may be required to support the stool, which may be undesirable for durability of the reusable bowl strainer 100.

Bowl strainer 400 may be formed of lightweight plastic or other suitable materials that are washable and re-usable as needed. Bowl strainer 400 may also be made of disposable materials for singular use in hospital, clinical or home use. The bowl-shaped frame 404 may have curved line cross-section 412 as shown in the illustrated embodiment of a bowl strainer 400 in FIGS. 4B, 4D and 4E. However, various other cross-sections, for example and not by way of limitation, straight line (not shown, but see 112 in FIGS. 1B, 1D and 1E), according to other contemplated embodiments.

FIGS. 5A-5E illustrate another embodiment of a hand-held urine strainer 500, according to the present invention. More particularly, FIGS. 5A-5E are perspective, top, side, front and handle-edge views, respectively, of the embodiment of a hand-held urine strainer 500. The embodiment of hand-held urine strainer 500 is similar to the embodiment of hand-held urine strainer 200. Hand-held urine strainer 500 is also configured for use while standing or squatting over a toilet bowl (not shown). Hand-held urine strainer 500 may be used by male and female patients. But, because of its shape, hand-held urine strainer 500 is particularly adapted for use by female patients. The hand-held urine strainer 500 is sized to be portable and is configured to reusable by simply washing in water. Additional features of the embodiment of hand-held strainer 500 follow.

Hand-held urine strainer 500 may have a generally bowl-shaped frame 204 with a handle 502 extending from a central end 520 of rim 514 at handle base 518. Rim 514 may have a generally rounded-rectangular-shape as viewed from the top in FIG. 5B. More particularly, rim 214 includes two opposed convex lips 516 located at central 520 and distal 522 ends. Rim 514 further includes two opposed concave lips 512 between the central 520 and distal 522 ends. The lips 512 and 516 of rim 514 are generally rounded and not sharp-edged. The two opposed concave lips 512 are specially adapted to fit, and may be held, between the thighs of a female patient during urination.

As noted above, hand-held urine strainer 500 may further include a protruding handle 502 extending from one of the two opposed convex lips 516 at central end 520. More particularly, the handle base 518 meet one of the two opposed convex lips 516 at the central end 520. According to the illustrated embodiment of hand-held urine strainer 500 a hole 526 may be formed near the proximate end 524 of handle 502, see FIGS. 5A-5D. Hole 526 may be used for hanging strainer 500 for storage or to dry after washing for reuse. According to various embodiments, handle 502 may be angled at a preselected angle, Φ, which is measured from a line perpendicular to the flat or planar surface of bottom end 528, see FIG. 5C. This preselected angle, Φ, may range from 0°-45° in order to facilitate placement of the hand-held urine strainer 500 comfortably during use.

In operation, hand-held urine strainer 500 is configured to be positioned for use with the bottom end 528 toward ground to take advantage of gravity. When positioned for use, hand-held urine strainer 500 is configured to gather urine inside the bowl-shaped frame 504 and guide it toward the recessed area in the center 510 of the hand-held urine strainer 200. During use, urine from a patient's urethra is directed toward the recessed area in the center 510.

Handle 502 may be used by the patient to control the placement of the hand-held strainer 500 during use. The generally bowl-shaped frame 504 of hand-held urine strainer 500 extends from the rim 514 down to the recessed area in the center 210 which forms the bottom end 528 of strainer 500. The recessed area in the center 510 may further include a generally D-shaped opening 506, see particularly FIGS. 5B and 5E. The D-shaped opening 506 located within the recessed center 510 may be covered with a flexible thin fine mesh 530 for straining fluid voids.

Handle 502 may extend from rim 514 and handle base 518. Handle 502 may be configured with any suitable shape and length according to various embodiments. More particularly, the shape and length of the handle 502 is specifically designed for female patients to avoid urinating on their own hand(s), or other body part, or on the toilet, or rim thereof, and to collect any items passed through the urine stream, but held back by fine mesh 530 such as kidney stones for analysis.

Figure 5F:
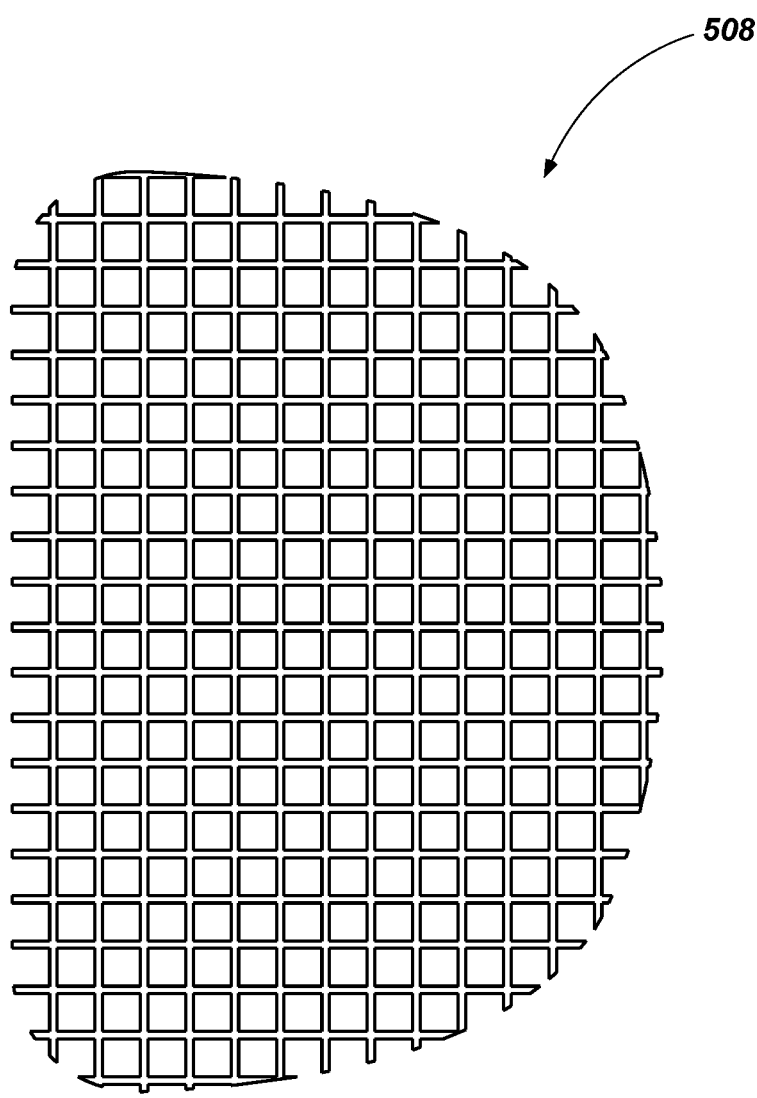
FIG. 5F is a plan view of an embodiment of a fine mesh feature of the embodiment of a hand-held urine strainer shown in FIGS. 5A-5E, according to the present invention.

FIG. 5F is a plan view of an embodiment of the flexible fine thin mesh 508 of the embodiment of a hand-held urine strainer 500 shown in FIGS. 5A-5E, according to the present invention. Mesh 508, like mesh 408 (FIG. 4F) may be formed of any suitable material that allows fluid (urine) to pass through the mesh 508 and into the toilet bowl or other urine receptacle, while retaining any items (kidney stones, etc.) contained in the urine stream. According to one embodiment, mesh 508 may be formed of 800 micron polypropylene mesh having 58% open area, with hole size 0.032"×0.032" and having thickness, 0.016". It will be understood that the particular dimensions of mesh 508 illustrated in FIG. 5F are configured to allow mesh 508 to cover opening 506. According to the illustrated embodiments, opening 506 and its corresponding mesh 508 are both generally "D-shaped" in plan view. However, it will further be understood that the particular shape of opening 506 and its corresponding mesh 508 may be of any suitable shape. Mesh 508 may be adhered to hand-held urine strainer 500 in any manner known to those skilled in the art including, for example and not by way of limitation, adhesive, thermal fusing, tape, etc.

Figure 6A:
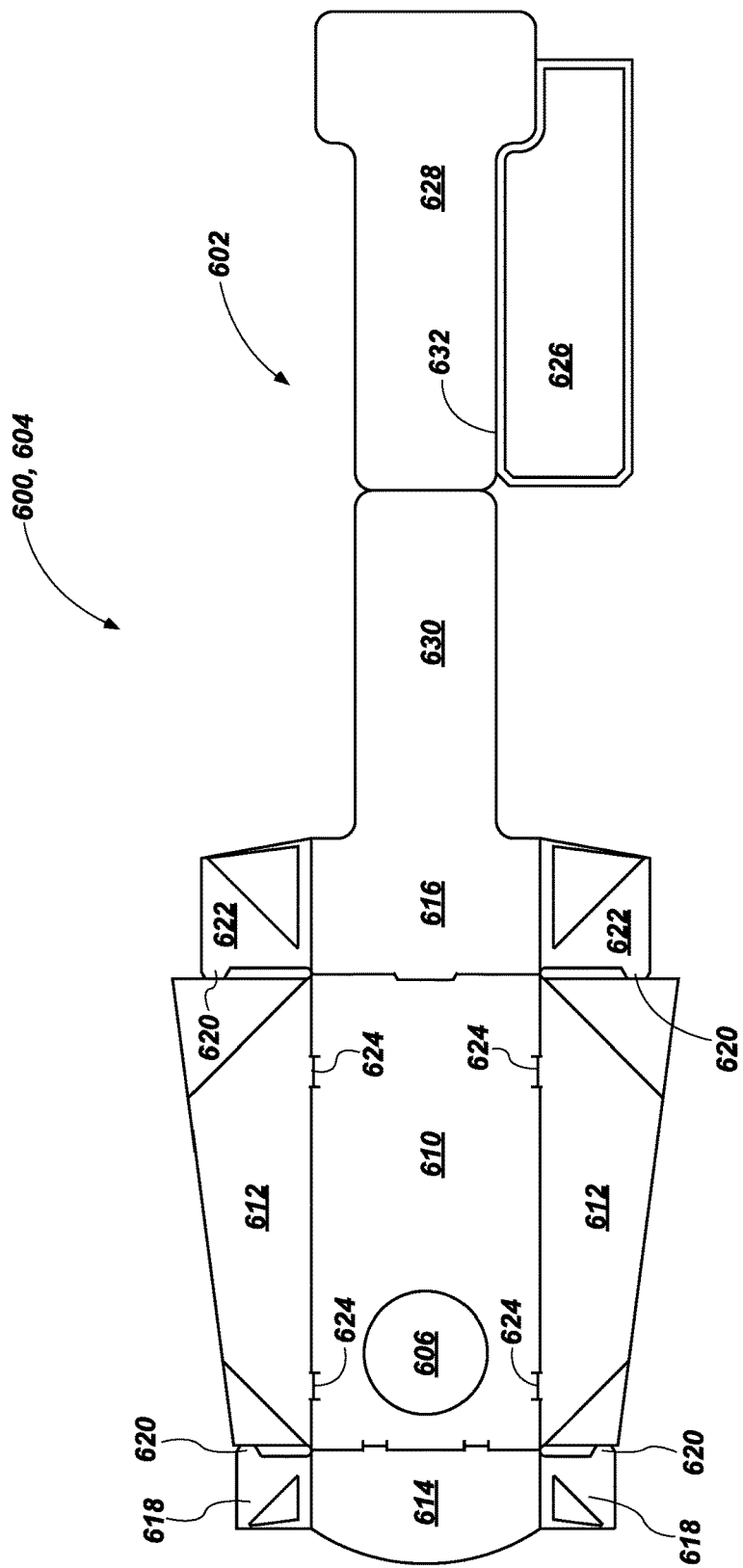
FIG. 6A is a plan view of an embodiment of a pattern for a disposable hand-held urine strainer, according to the present invention.
Figure 6B:
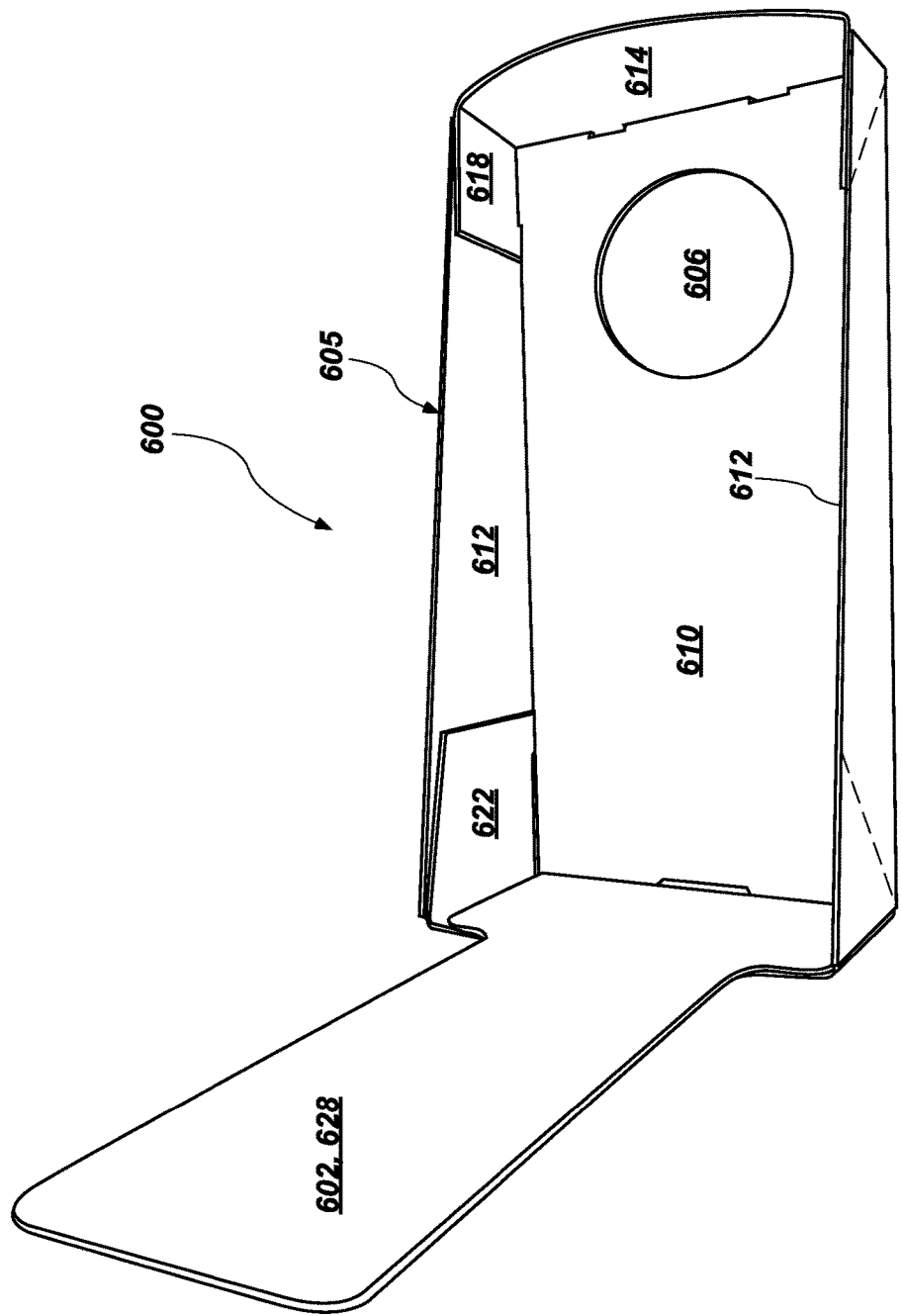
FIGS. 6B and 6C are left perspective and right side views of the embodiment of a disposable hang-held urine strainer as cut and folded from the pattern shown in FIG. 6A.
Figure 6C:
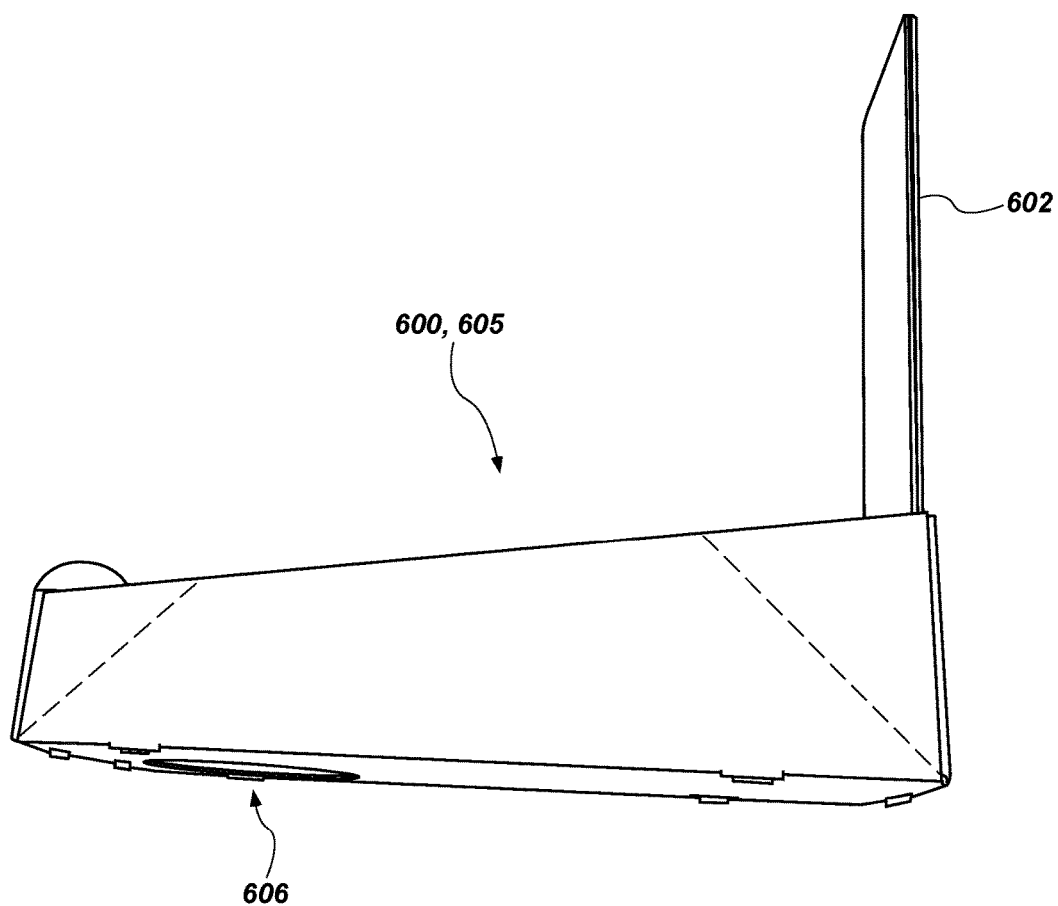

Another embodiment of a hand-held urine strainer 600 is disclosed. FIG. 6A is a plan view of an embodiment of pattern, shown generally at arrow 604, for a disposable hand-held urine strainer 600, according to the present invention. The embodiment of a pattern 604 for strainer 600 is configured to be cut from lightweight milled paper or cardboard and folded into the shape or assembled frame 605 shown in FIGS. 6B and 6C. More particularly, FIGS. 6B and 6C are left perspective and right side views of the embodiment of a frame 605 for a disposable hand-held urine strainer 600 as cut and folded from the pattern 604 shown in FIG. 6A, but without a fine mesh 608 placed over the circular opening 606. Accordingly, this embodiment of a disposable hand-held urine strainer 600 may be formed of essentially two separate components, (1) a pattern 604 that is folded into an assembled frame 605 having a circular opening 606 and (2) a fine mesh 608 placed over the circular opening 606.

Adhesives may further be used to hold the folded pattern 604 together along with cut-outs and tabs in various locations in order to obtain assembled frame 605. However, the entire strainer 600 is configured to be simply folded into the shape shown in FIGS. 6B and 6C. Once folded, strainer 600 may be used by a patient to strain urine during bladder elimination. Then kidney stones (if any) may be retrieved from within the strainer basin for further analysis and then strainer 600 may be disposed in a waste receptacle.

As noted above, a completed embodiment of a disposable urine strainer 600 further includes a fine mesh 608 (not shown in FIGS. 6A-6C) placed over the circular opening 606. According to one embodiment, mesh 608 may be formed of 800 micron polypropylene mesh having 58% open area, with hole size 0.032"×0.032" and having thickness, 0.016". According to another embodiment, mesh 608 may be circular in shape and sized to cover opening 606. However, mesh 608 may be any shape, e.g., square, rectangular, etc., that is large enough to cover opening 606, according to still other embodiments. Mesh 608 may be adhered to disposable urine strainer 600 in any manner known to those skilled in the art including, for example and not by way of limitation, adhesive, thermal fusing, tape, etc.

As further shown in FIG. 6A, an embodiment of pattern 604 for a disposable urine strainer 600 may further include a generally rectangular-shaped floor panel 610 in which an opening 606 and four slots 624 are cut. The embodiment of a pattern 604 for a disposable urine strainer 600 may further include opposed side panels 612, a front panel 614 and rear panel 616. More particularly, the front panel 614 may further include opposed front corner panels 618 each having a tab 620. Similarly, the rear panel 616 may further include opposed rear corner panels 622, each having a tab 620. During assembly of disposable urine strainer 600, panels 612, 614 and 616 are folded in toward circular opening 606 on floor panel 610, with corner panels 618 and 622 inside side panels 612 such that tabs 620 may be inserted in to slots 624. In this folded and tab-slotted configuration the frame 605 of disposable urine strainer 600 is essentially assembled.

An embodiment of handle, shown generally at arrow 602, may include first, second and third panels 626, 628 and 630, respectively. During assembly, a partial cut 632 (see FIG. 6A) between the first 626 and second 628 panels allows the first panel 626 to be folded up onto the second panel 628 followed by folding first and second panels 626 and 628 onto third panel 630. By folding first through third panels 626, 628 and 630 on top of each other, handle 602 acquires added torsional stiffness for use as a handle during use.

Though FIGS. 6A-6C illustrate an assembled frame 605 (namely, a strainer 600 without mesh 608) it will be understood that by simply adhering mesh 608 over opening 606, a complete strainer 600 is obtained. The dimensions of the embodiment of pattern 604 are merely exemplary and not critical to the functioning of the strainer 600. Accordingly, it will be understood that any of the dimensions and features disclosed may be varied to any suitable degree as long as the resulting strainer 600 is sized for use by a patient to strain urine, according to other embodiments of the present invention.

Figure 6D:
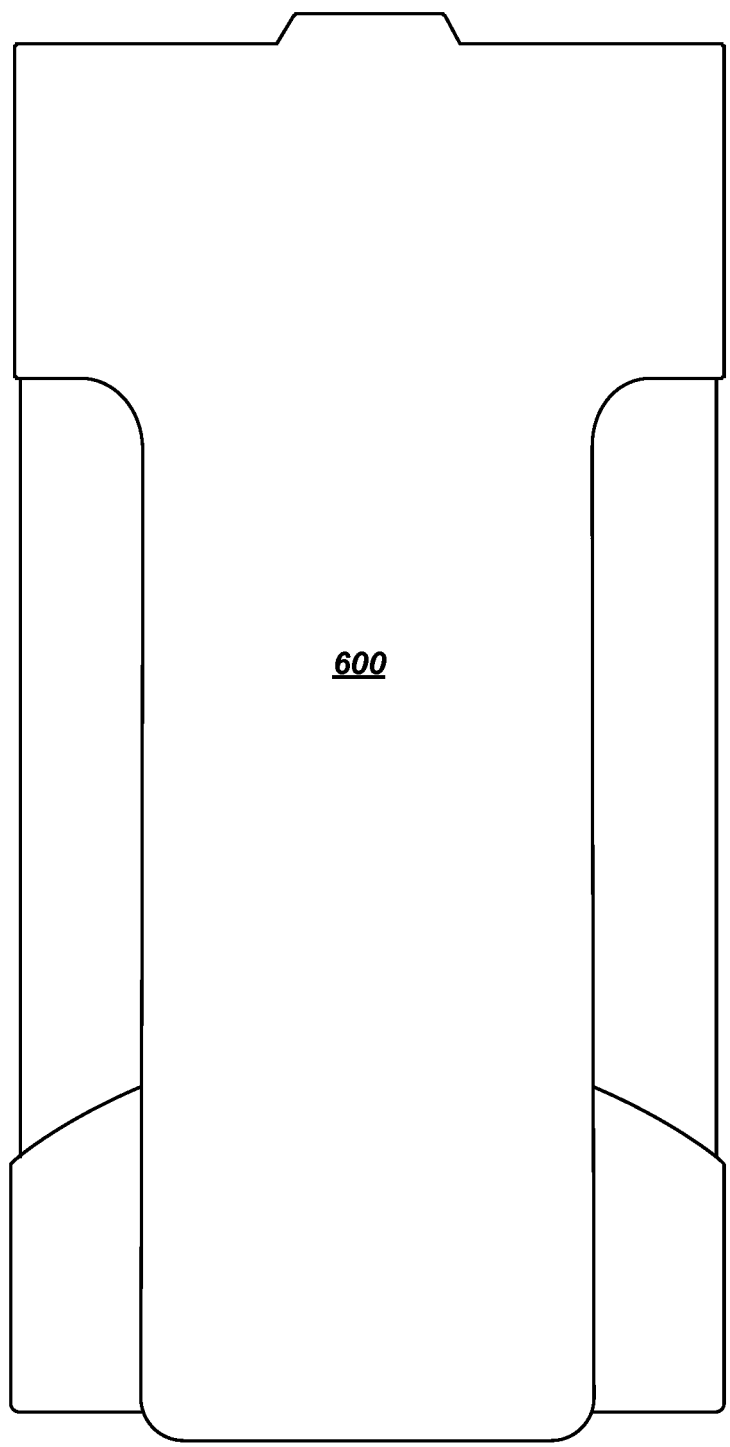
FIG. 6D is a perspective view of an embodiment of a disposable urine strainer shown in FIGS. 6A-6C, folded for storage, according to the present invention.

A particularly useful feature of disposable urine strainer 600 is that it can be folded nearly flat and conveniently packaged for retail sale or carried by the user. FIG. 6D is a perspective view of an embodiment of a disposable urine strainer 600 shown in FIGS. 6A-6C, folded for storage, according to the present invention. As shown in FIG. 6D, pattern 604 may be folded as shown, and later unfolded and assembled into the frame 605 shown in FIGS. 6B and 6C. It will also be understood that a plurality of folded disposable urine strainers 600 may be packaged in an appropriately sized box for carrying by the user. An appropriate box size may be configured to carry any suitable number of folded strainers 600, for example and not by way of limitation, 2-12 strainers 600. By having a portable supply of urine strainers 600, the user can have ready access strainers 600 to strain urine while traveling or away from home.

The embodiments of urine strainers 100, 200, 300, 400, 500 and 600 disclosed above are all useful for straining urine and are particularly useful for female patients because of the inherent anatomical difficulty in directing a urine stream. But, it will be understood that male patients can also use any one of the embodiments of urine strainers 100, 200, 300, 400, 500 and 600 disclosed above. The hand-held urine strainer embodiments 200, 300, 500 and 600 disclosed above are particularly useful in preventing the undesirable possibility of urinating on one's own hands or fingers during bladder elimination, because of the respective handles 202, 302, 502 and 602 that hold the catch-basin and strainers away from the patient's urethra and urine stream during elimination. For this very same reason, it is desirable to have a urine sampler with a handle that serves the same function, but in the context of obtaining a urine sample, rather than straining the urine to obtain a particular residue. An embodiment of such a urine sampler will now be disclosed.

Figure 7A:
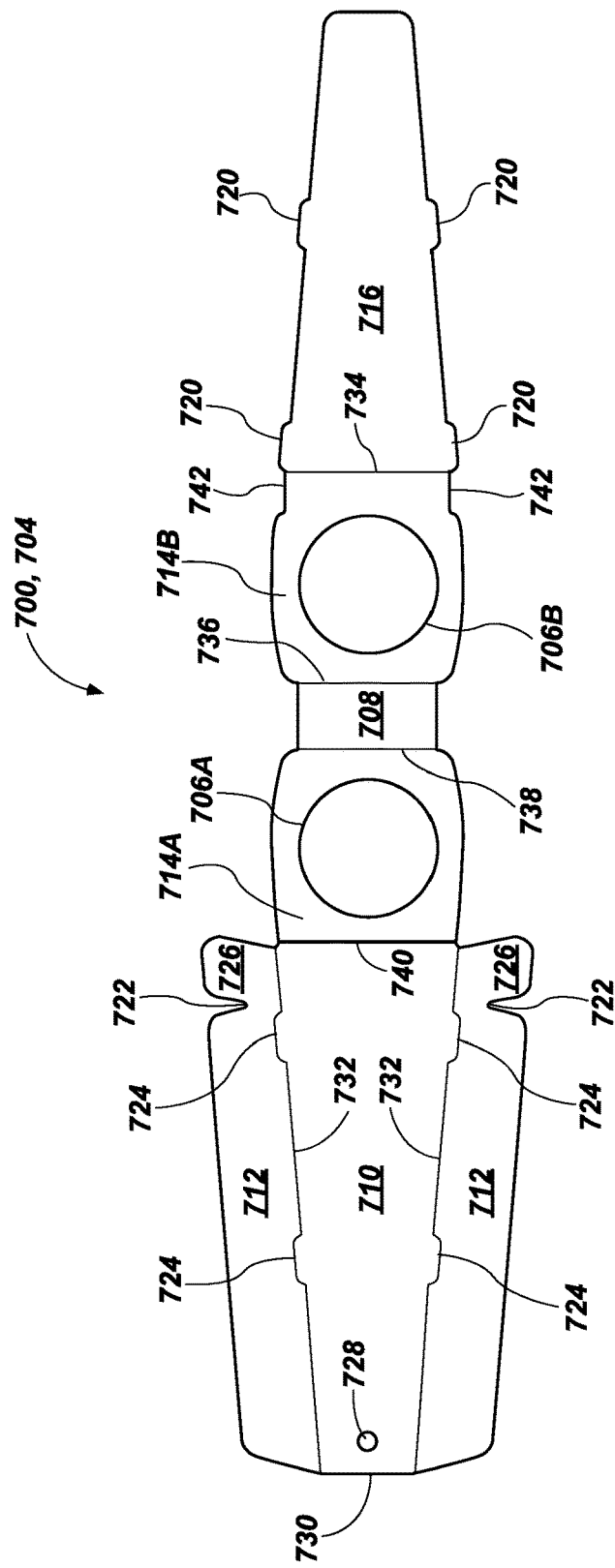
FIG. 7A is a plan view of an embodiment of a pattern for a disposable hand-held urine sampler after it has been cut from lightweight milled paper or cardboard, according to the present invention.

FIG. 7A is a plan view of an embodiment of a pattern 704 for a disposable hand-held urine sampler 700, according to the present invention. The embodiment of a pattern 704 for sampler 700 is configured to be cut from lightweight milled paper or cardboard as shown in FIG. 7A.

As further shown in FIG. 7A, an embodiment of pattern 704 for a disposable urine sampler 700 may further include a handle floor panel 710 in which four slots 724 are cut. The embodiment of a pattern 704 for a disposable urine sampler 700 may further include opposed side panels 712, a bridge panel 708 located between first and second cup holder panels 714A and 714B and handle ceiling panel 716 adjacent to second cup holder panel 714B. The embodiment of a handle ceiling panel 716 may further include four tabs 720 each corresponding to a respective slot 724. Embodiments of opposed side panels 712 may each have notches 722 located near the first cup holder panel 714A. The notches 722 define finger tabs 726 adjacent to first cup holder panel 714A. Second cup holder panel 7148 may also be configured with cutouts 742 adjacent to handle ceiling panel 716 and fold line 734. According to the embodiment of pattern 704 illustrated in FIG. 7A, a hole 728 may be formed in the proximate end 730 of handle floor panel 710.

Pattern 704 is configured to be assembled by folding and tucking tabs 720 into corresponding slots 724. More particularly, opposed side panels 712 are configured to be folded in toward handle floor panel 710 at fold lines 732 located between opposed side panels 712 and the handle floor panel, thus opening slots 724. Handle ceiling panel 716 is configured to be folded toward handle floor panel 710 at fold line 734 located between the handle floor panel 710 and second cup holder panel 714B. Second cup holder panel 714B may be configured to fold toward handle floor panel 710 at fold lines 736 and 738. Finally, first cup holder panel may be configured to fold toward handle floor panel 710 and fold line 740.

Figure 7B:
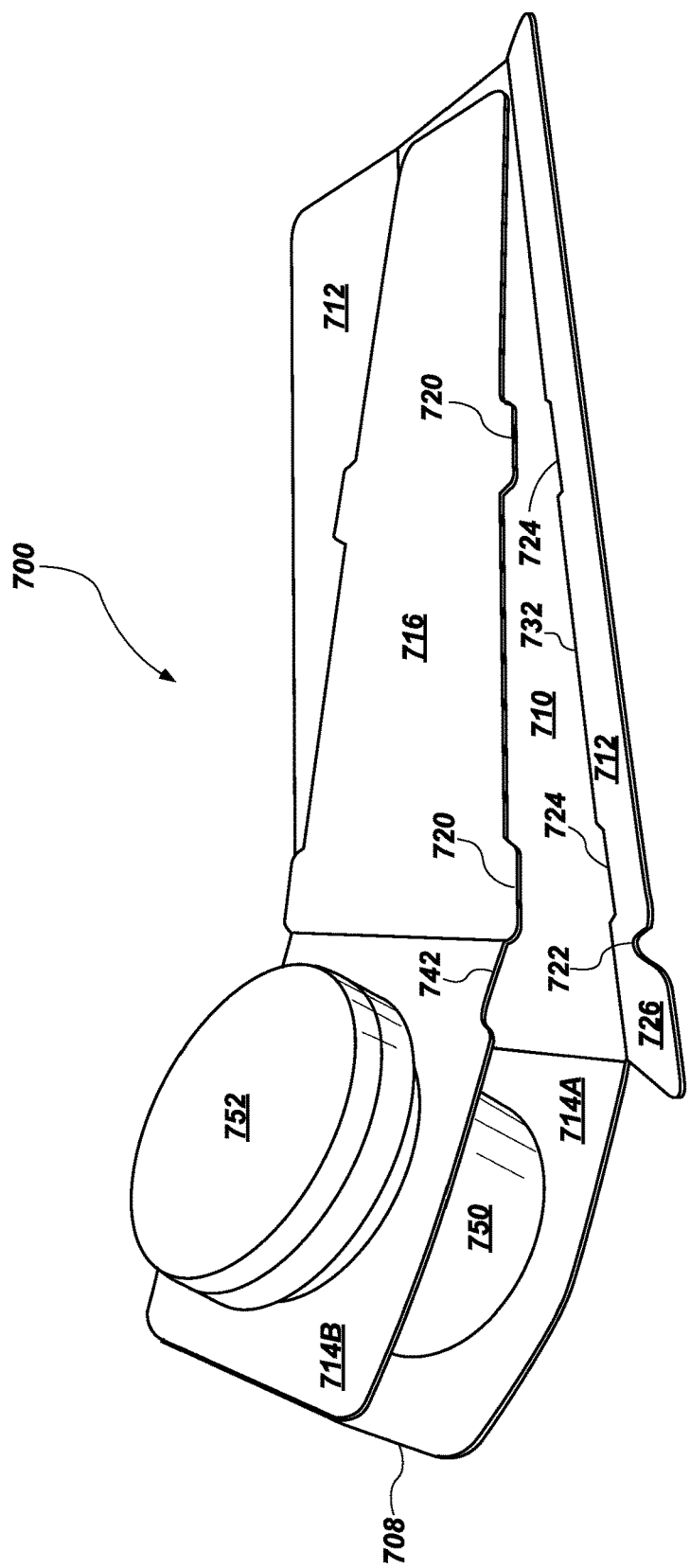
FIG. 7B illustrates a perspective image of the embodiment of the disposable hand-held urine sampler shown in FIG. 7A, folded with a urine sample cup placed through first and second circular openings, according to the present invention.
Figure 7C:
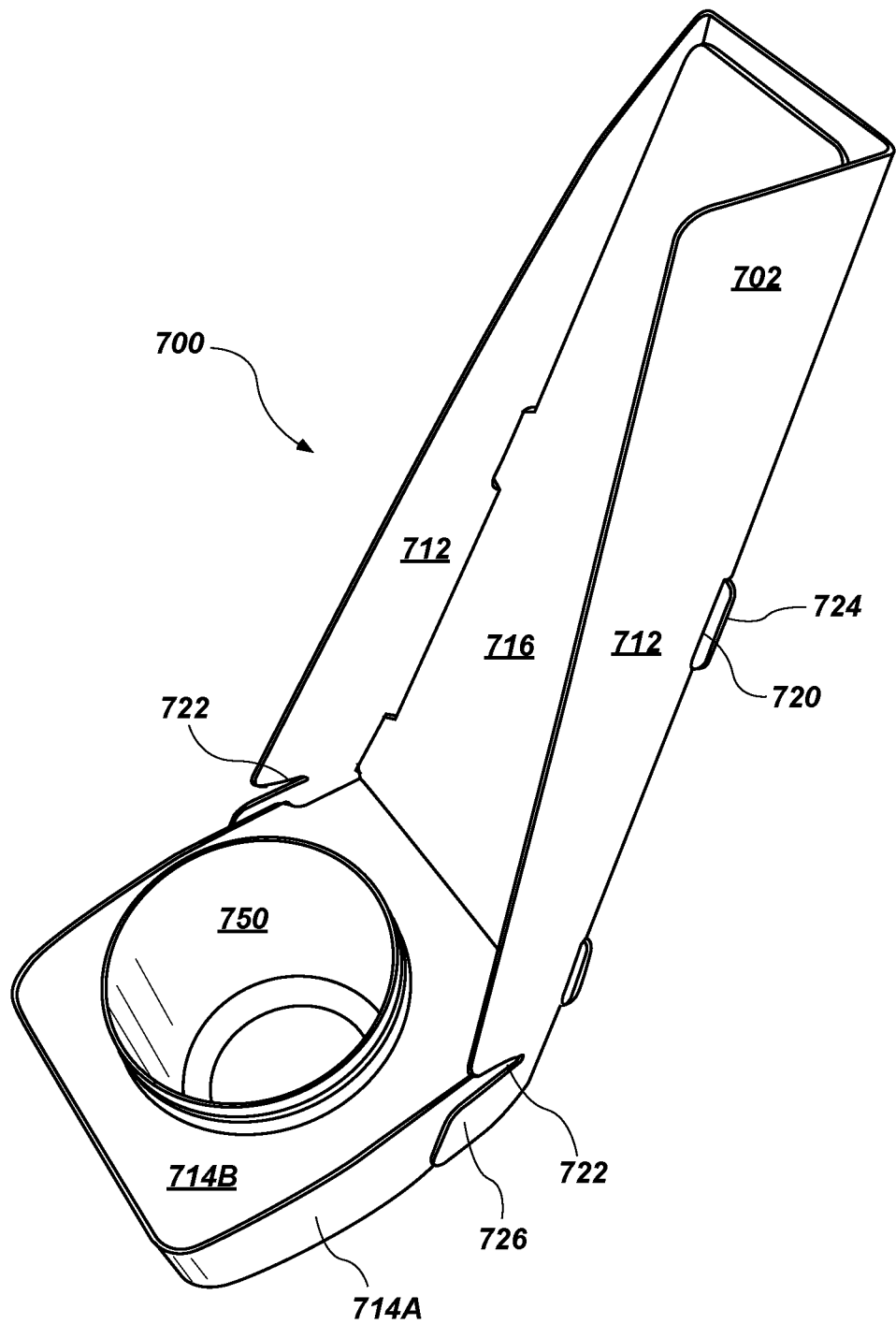
FIG. 7C illustrates another perspective image of the embodiment of the disposable hand-held urine sampler shown in FIGS. 7A-7B, completely folded and ready to use with urine sample cup cap removed.

FIG. 7B illustrates a perspective image of the embodiment of a disposable hand-held urine sampler 700 shown in FIG. 7A, folded with a urine sample cup 750 placed through first and second circular openings 706A and 706B, according to the present invention. As shown in FIG. 7C, handle ceiling panel 716 overlays handle floor panel 710 with slots 724 aligned with tabs 720. As further shown in FIG. 7B, first and second cup holder panels 714A-B are generally parallel to each other and separated by bridge panel 708. Additionally, first and second circular openings 706A-B are aligned by urine sample cup 750. This configuration of disposable hand-held urine sampler 700 provides stable support to urine sample cup 750.

FIG. 7C illustrates another perspective image of the embodiment of the disposable hand-held urine sampler 700 shown in FIGS. 7A-7B, completely folded and ready to use with urine sample cup cap 752 removed. Finger tabs 726 may be folded in toward cup 750 as facilitated by notches 722, thereby holding first and second cup holder panels 714A-B generally parallel to each other in tandem with bridge panel 708.

Handle 702 may be used to grip the sampler 700 shown in FIG. 7C during use. In practice, the embodiment of a disposable hand-held urine sampler 700 is held by handle 702 to capture urine from the user/patient within urine sample cup 750. After sufficient urine is filled within urine sample cup 750, cap 752 may be placed on cup 750 to seal and the sampler 700 discarded. Because of the elongated handle 702 there is less risk of the patient urinating on their own hands/fingers.

Figure 8A:
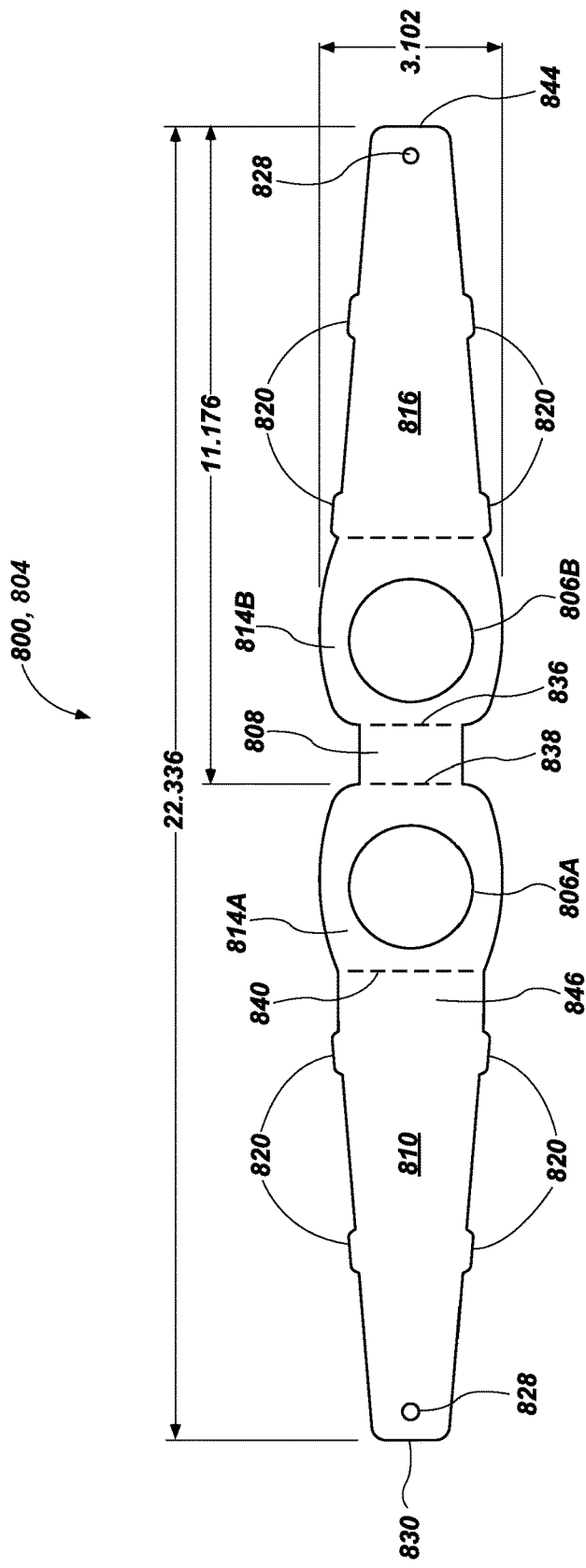
FIG. 8A is a plan view of another embodiment of a disposable hand-held-urine sampler, according to the present invention.
Figure 8B:
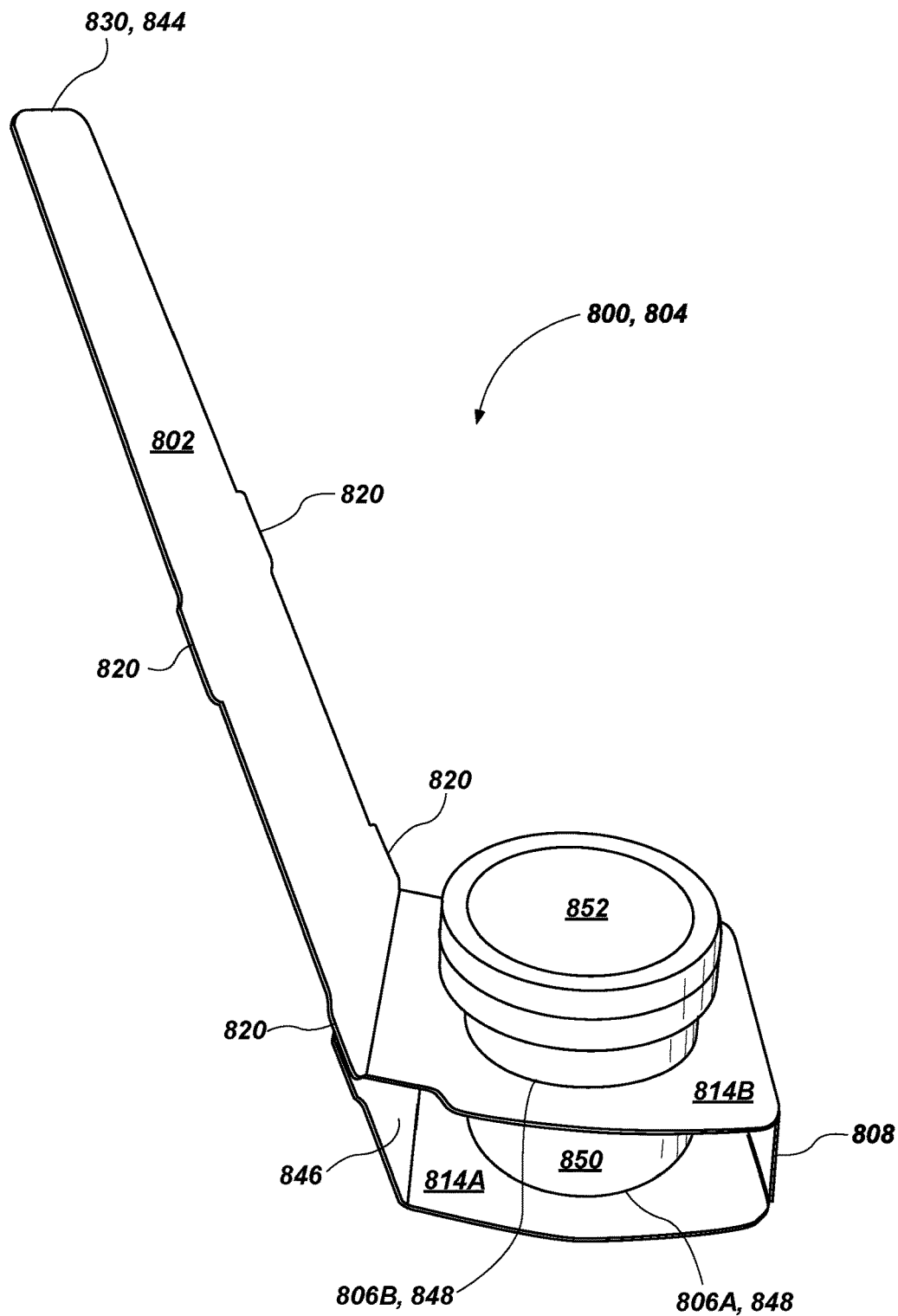
FIG. 8B is a perspective view of the embodiment of the disposable hand-held-urine sampler shown in FIG. 8A, according to the present invention.

FIGS. 8A and 8B are plan and perspective views of another embodiment of a disposable hand-held-urine sampler, according to the present invention. More particularly, FIG. 8A illustrates pattern or frame 804 used to form disposable hand-held urine sampler 800. The terms "pattern" and "frame" are used interchangeably herein. However, it will be understood that as described herein, a pattern place on or cut from lightweight paper or cardboard stock is used to form the frame. The frame may be folded along fold lines that are identified in the pattern according to various embodiments herein. FIG. 8B illustrates a perspective view of the embodiment of a pattern 804 for sampler 800 after it has been cut from lightweight milled paper or cardboard, folded and then glued together to form a handle 802 and sample cup receptacle 848 formed coaxially aligned first and second circular openings 806A-B. FIG. 8B illustrates sampler 800 after it has been cut from lightweight milled paper or cardboard. This embodiment of sampler 800 is similar to sampler 700, except simpler in that the opposed side panels 712, and other features, have been removed in their entirety.

As further shown in FIG. 8A, an embodiment of pattern, shown generally at arrow 804 for a disposable urine sampler 800 may further include a handle floor panel 810 with proximate end 830. The embodiment of a pattern 804 for a disposable urine sampler 800 may further include a bridge panel 808 located between first and second cup holder panels 814A and 814B and handle ceiling panel 816 adjacent to second cup holder panel 814B. The embodiment of a handle ceiling panel 816, having a distal end 844, may further include four tabs 820 each corresponding to four respective tabs 820 located on handle floor panel 810.

According to the embodiment of pattern 804 illustrated in FIGS. 8A and 8B, a holes 828 may be formed near the proximate end 830 of handle floor panel 810 and the distal end 844 of handle ceiling panel 816. Disposable urine sampler 800 may be assembled from pattern 804 by: (1) folding handle ceiling panel 816 toward second cup holder panel 814B at first fold line 834, (2) folding second cup holder panel 814B toward bridge panel 808 at second fold line 836, (3) folding the bridge panel 808 toward the first cup holder panel 814A at third fold line 838, folding first cup holder panel 814A toward handle floor panel 810 at fourth fold line 840, and (5) applying an adhesive between handle floor panel 810 and handle ceiling panel 816 such that when pressed together a handle 802 is formed, see FIG. 8B.

According to the illustrated embodiment of sampler 800, handle has proximate 830 and distal 844 ends of handle floor and ceiling panels 810 and 816, respectively, adjacent to one another and the four tabs 820 of handle floor panel 810 aligned with the four tabs 820 of handle ceiling panel 816. It will be understood that other handle configurations or embodiments are also possible, for example and not by way of limitation, a handle that has no tabs at all (not shown), a handle that does not taper (not shown) from urine sample cup receptacle 848 to the aligned proximate 830 and distal 844 ends. According to the illustrated embodiment, handle 802 shown in FIG. 8B tapers from urine sample cup receptacle 848 to the aligned proximate 830 and distal 844 ends.

As shown in FIG. 8B, a urine sample cup 850, with (as shown) or without urine sample cup cap 852 may be placed in a sample cup receptacle 848 formed by the first and second circular openings 806A and 806B that are aligned with centers passing through an axis (not shown) of the cup 850. The assembled disposable hand-held urine sampler 800 shown in FIG. 8B, shows first and second cup holder panels 814A-B to be parallel to each other and separated by bridge panel 808 and a corresponding portion 846 of handle floor panel 810. The corresponding portion 846 may be located between fold line 840 and two tabs 820 located on handle floor panel 810, according to the illustrated embodiment.

Figure 8C:
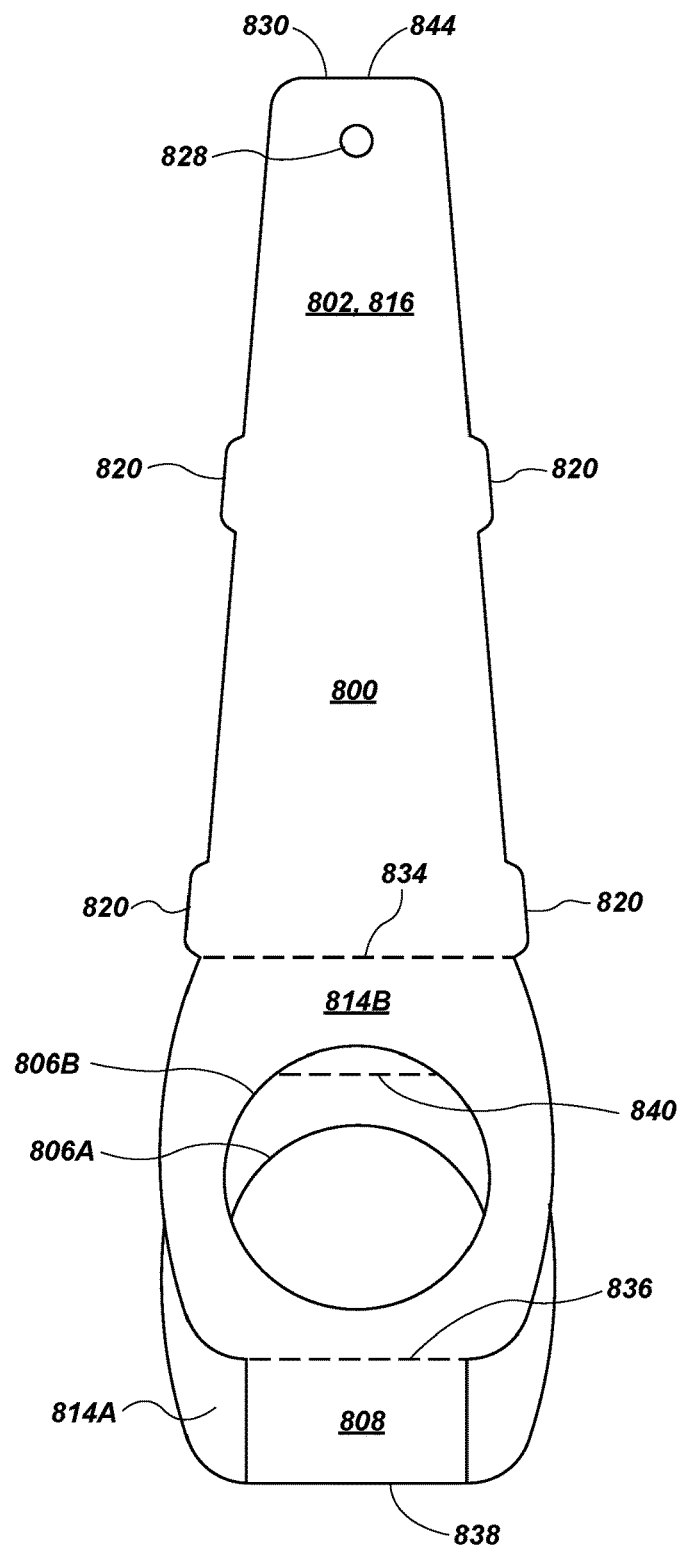
FIG. 8C is a top view of the disposable hand-held-urine sampler shown in FIGS. 8A and 8B, folded flat, according to the present invention.

FIG. 8C is a top view of the disposable hand-held-urine sampler 800 shown in FIGS. 8A and 8B, folded flat, according to the present invention. Pre-glued versions of disposable hand-held urine sampler 800 may be folded at second fold line 836 with handle floor 810 and ceiling 816 panels adhered together (using glue, staples or any other means for adhering the two panels 810 and 816 together). Pre-glued versions of disposable hand-held urine sampler 800 folded as shown in FIG. 8C may be stacked and stored in bulk or otherwise packaged for shipping and storage.

In order to use folded sampler 800, the other three fold lines, 834, 838 and 840 are engaged to separate the first and second cup holder panels 814A-B from one another in a parallel configuration thus aligning first and second circular openings 806A-B to form a receptacle 848 for receiving urine sample cup 850, see FIG. 8B. During use a cup 850 without cap 852 is placed within receptacle 848, the user grasps the handle 802, places the cup 850 adjacent to the user's urethra (not shown) and delivers the desired measure of urine into the cup without concern for urinating on the user's hands because of the extended handle 802. The cup 850 can then be capped 852 and delivered to the lab for analysis as needed.

Structural features of the embodiments of bowl strainers 100 and 400 and hand-held urine strainers 200 and 500 may be formed of any suitable material, for example and not by way of limitation, lightweight plastic, or plastic-like material which is washable and re-usable as needed. Disposable urine strainer 600 and urine samplers 700 and 800 may be formed of any suitable material, for example and not by way of limitation, lightweight milled paper or cardboard for low cost and eco-friendly waste decomposition. Note that the embodiments of urine strainers 100, 200, 300, 400, 500, 600 and samplers 700 and 800 disclosed herein may have any suitable dimensions. The particular dimensions illustrated in the drawings are merely exemplary and not intended to limit the scope of the present invention. Having described particular embodiments of the urine strainers 100, 200, 300, 400, 500, 600 and urine samplers 700 and 800 disclosed above, generic embodiments will now be described.

An embodiment of a urinary bowl strainer is disclosed. The embodiment of a urinary bowl strainer may include a bowl-shaped frame having an opening covered by mesh. According this embodiment, the mesh may be configured to pass urinary fluid but retain solids. The embodiment of a urinary bowl strainer may include a plurality of support members extending from the bowl-shaped frame. According to one embodiment, the plurality of bowl-shaped members may be configured to rest on a top surface of a toilet bowl basin. According to a particular embodiment of a urinary bowl strainer, the mesh may be formed of 800 micron polypropylene mesh having 58% open area, with hole size 0.032"×0.032" and having thickness, 0.016". According to another embodiment of the urinary bowl strainer, the plurality of support members may be four support members each configured to rest on the top surface of a toilet bowl basin and underneath a toilet seat. According to yet further embodiments of the urinary bowl strainer, the shape of the opening may be circular, oval-shaped, or D-shaped when viewed in plan view.

An embodiment of a hand-held urine strainer is disclosed. The embodiment of a hand-held urine strainer may include a bowl-shaped frame having a rim. According to this embodiment, the rim may include opposed concave lips configured for placement between thighs of a user. According to this embodiment, there may be an opening below the rim with a mesh covering the opening. The embodiment of a hand-held urine strainer may further include a handle extending from the rim. According to additional embodiments of the hand-held urine strainer, the shape of the opening may be circular, oval-shaped, or D-shaped. According to a particular embodiment of a hand-held urine strainer, the mesh may be formed of 800 micron polypropylene mesh having 58% open area, with hole size 0.032"×0.032" and having thickness, 0.016".

An embodiment of a disposable hand-held urine strainer is disclosed. The embodiment of a disposable hand-held urine strainer may include a pattern configured to be folded into an assembled frame having an opening. According this embodiment of the disposable hand-held urine strainer, the opening may be covered by mesh. According to this embodiment, the mesh may be configured to pass urinary fluid but retain solids. According to one embodiment of the disposable hand-held urine strainer, the foldable frame may further include a basin and a handle extending from the basin. According to yet another embodiment of a disposable hand-held urine strainer, the basin may further include a rectangular floor panel, opposed side panels extending from the floor panel, a front panel extending from the floor panel and a rear panel extending from the floor panel and opposed to the front panel. According to still another embodiment of a disposable hand-held urine strainer, the handle may include a first panel, a second panel adjacent to the first panel and a first fold line between the first and the second panels and a third panel adjacent to the second panel and a second fold line between the second and third panels. According to yet still another embodiment of a disposable hand-held urine strainer, the first panel may be configured to be folded on top of the second panel along the first fold line. According to another embodiment of a disposable hand-held urine strainer, the first and second panels may be configured to be folded on top of the third panel along the second fold line. According to one embodiment of a disposable hand-held urine strainer, the mesh may be formed of 800 micron polypropylene mesh having 58% open area, with hole size 0.032"×0.032" and having thickness, 0.016". According to other embodiments, a disposable hand-held urine strainer may be formed of lightweight milled paper or cardboard.

An embodiment of a disposable hand-held urine sampler is disclosed. The embodiment of a disposable hand-held urine sampler may include a frame cut along a pattern from lightweight milled paper or cardboard and folded to form an assembled frame for supporting a urine sample cup. According to one embodiment, the frame may further include a handle floor panel having a proximate end. The embodiment of a frame may further include a first cup holder panel extending from handle floor panel along a first fold line and including a first circular opening. The embodiment of a frame may further include a bridge panel extending from the first cup holder panel along a second fold line. The embodiment of a frame may further include a second cup holder panel extending from the bridge panel along a third fold line and including a second circular opening. The embodiment of a frame may further include a handle ceiling panel having a distal end. According to this embodiment, the handle ceiling panel may extend from the second cup holder panel along a fourth fold line.

According to another embodiment, the disposable hand-held urine sampler may further include opposed side panels extending from the handle floor panel along respective opposing fold lines. According to yet another embodiment of the disposable hand-held urine sampler, the handle floor panel may be adhered to the handle ceiling panel with the proximate and distal ends adjacent one another by folding along the second fold line only, thereby forming a handle. According to still another embodiment of the disposable hand-held urine sampler, the first cup holder panel may be separated and parallel to the second cup holder panel by further folding along the first, third and fourth fold lines. According to still yet another embodiment of the disposable hand-held urine sampler, a urine sample cup may be placed through the first and second circular openings. According to a particular embodiment the disposable hand-held urine sampler may be formed of lightweight milled paper or cardboard.

While the foregoing advantages of the present invention are manifested in the illustrated embodiments of the invention, a variety of changes can be made to the configuration, design and construction of the invention to achieve those advantages. For example, the tabs 820 shown on the handle 802 of sampler 800 (see FIGS. 8A-8C) may be removed in their entirety according to an alternative embodiment, with essentially the same functionality. Hence, reference herein to specific details of the structure and function of the present invention is by way of example only and not by way of limitation.

What is claimed is:
1. A disposable hand-held urine strainer, comprising:
   a pattern configured to be folded into an assembled frame having an opening, the opening covered by mesh, the mesh configured to pass urinary fluid but retain solids, the foldable frame further comprising:

a basin; and a handle extending from the basin.

2. The disposable hand-held urine strainer according to claim 1, wherein the basin further comprises:
   a rectangular floor panel;
   opposed side panels extending from the floor panel;
   a front panel extending from the floor panel; and
   a rear panel extending from the floor panel and opposed to the front panel.

3. The disposable hand-held urine strainer according to claim 2, wherein the handle further comprises:
   a first panel;
   a second panel adjacent to the first panel and a first fold line between the first and the second panels; and
   a third panel adjacent to the second panel and a second fold line between the second and third panels.

4. The disposable hand-held urine strainer according to claim 3, wherein the first panel is configured to be folded on top of the second panel along the first fold line.

5. The disposable hand-held urine strainer according to claim 4, wherein the first and second panels are configured to be folded on top of the third panel along the second fold line.

6. The disposable hand-held urine strainer according to claim 1, wherein the mesh further comprises 800 micron polypropylene mesh having 58% open area, with hole size 0.032"×0.032" and having thickness, 0.016".

7. The disposable hand-held urine strainer according to claim 1, further comprised of lightweight milled paper or cardboard.

8. A disposable hand-held urine sampler, comprising:
   a frame cut along a pattern from lightweight milled paper or cardboard and folded to form an assembled frame for supporting a urine sample cup, the frame further comprising:
   a handle floor panel having a proximate end;
   a first cup holder panel extending from handle floor panel along a first fold line and including a first circular opening;
   a bridge panel extending from the first cup holder panel along a second fold line;
   a second cup holder panel extending from the bridge panel along a third fold line and including a second circular opening; and
   a handle ceiling panel having a distal end, the handle ceiling panel extending from the second cup holder panel along a fourth fold line.

9. The disposable hand-held urine sampler according to claim 8, further comprising opposed side panels extending from the handle floor panel along respective opposing fold lines.

10. The disposable hand-held urine sampler according to claim 8, wherein the handle floor panel is adhered to the handle ceiling panel with the proximate and distal ends adjacent one another by folding along the second fold line only, thereby forming a handle.

11. The disposable hand-held urine sampler according to claim 10, wherein the first cup holder panel is separated and parallel to the second cup holder panel by further folding along the first, third and fourth fold lines.

12. The disposable hand-held urine sampler according to claim 11, wherein a urine sample cup may be placed through the first and second circular openings.

13. The disposable hand-held urine sampler according to claim 10, further comprising a first hole formed near the proximate end of handle floor panel and a second hole form near the distal end of the handle ceiling panel, the first and second holes aligned concentrically once folded to form the handle.

* * * * *